(12) United States Patent
James et al.

(10) Patent No.: US 6,664,407 B2
(45) Date of Patent: Dec. 16, 2003

(54) ELECTROCHEMICAL SACCHARIDE SENSOR

(75) Inventors: Tony D. James, Radstock (GB); Susumu Arimori, Iizuka (JP)

(73) Assignee: Beckman Coulter, Inc., Fullerton, CA (US)

( * ) Notice: Subject to any disclaimer, the term of this patent is extended or adjusted under 35 U.S.C. 154(b) by 79 days.

(21) Appl. No.: 10/060,790

(22) Filed: Jan. 30, 2002

(65) Prior Publication Data

US 2002/0164671 A1 Nov. 7, 2002

Related U.S. Application Data

(63) Continuation-in-part of application No. 09/729,332, filed on Dec. 4, 2000, now Pat. No. 6,387,672.

(51) Int. Cl.[7] ........................ C07F 17/02; A61K 31/295; C12Q 1/54
(52) U.S. Cl. ........................ 556/7; 556/143; 556/144; 435/14; 514/502
(58) Field of Search ........................ 556/7, 143, 144; 514/502; 435/14

(56) References Cited

U.S. PATENT DOCUMENTS

| | | | | |
|---|---|---|---|---|
| 5,803,770 | A | 9/1998 | Swendson et al. | 252/301.16 |
| 6,387,672 | B1 * | 5/2002 | Arimori et al. | 435/183 |
| 2003/0032202 | A1 * | 2/2003 | Stolowitz et al. | 436/518 |
| 2003/0082663 | A1 * | 5/2003 | Daniloff et al. | 435/14 |

OTHER PUBLICATIONS

U.S. patent application Ser. No. 09/729,332, Arimori et al., filed Dec. 4, 2000.
Samankumara, K.R.A. et al., *Two Dimensional Photoinduced Electron Transfer (PET) Fluorescence Sensor*, Chemistry Letters (1995), 503–504.
Moore, N.J. et al., *Redox Switching of carbohydrate binding to ferrocene boronic acid*, Can. J. Chem. 77:681–686 (1999).
Ori, Alichiro et al., *Electrochemical Detection of Saccharides by the Redox Cycle of a Chiral ferrocenylboronic Acid Derivative: a Novel Method for Sugar Sensing*, J. Chem. Soc., Chem. Commun., (1995), 1771–1772.
Hartley, James H., et al., *Synthetic receptors*, J. Chem. Soc., Perkin Trans. 1, (2000), 3155–3184.
Mizuno, T. et al., "Re–investigation of optical sensign properties of boronic–acid–appended Rel complexes for saccharides, "Database CAPLUS on STN, *Chemical Abstracts* (Columbus OH USA), CA:132:334675, Perkin 1, No. 3, pp. 407–413, 2000.
Murakami, H. et al., "Sugar sensign Utliizing aggregation properties of boronic–acid–appended prophyrins and metalloporhyrins," Database CAPLUS on STN, *Chemical Abstracts*(Columbus OH USA), CA:121:148059, Journal of the Chemical Society, Perin Transactions, No. 5, pp. 975–81, 1994.
Takeuchi, M., "Chirality Sensign Saccharides using a boronic acid–appended chiral ferrocane derivative," Database CAPLUS on STN, *Chemical Abstracts*, (Columbus OH USA), CA:134;71770, Tetrahedron:Asyhmetry 11, No. 16, pp. 3311–3322, 2000.
PCT Authority, "Notification of Transmittal of the International Search Report of the Declaration," PCT Application: No. PCT/US03/02915, dated Jun. 25, 2003, 6 pages.

* cited by examiner

Primary Examiner—Porfirio Nazario-Gonzalez
(74) Attorney, Agent, or Firm—Sheldon & Mak; William H. May; D. David Hill

(57) ABSTRACT

The invention provides compounds for detecting saccharides by electrochemistry. The compounds have a structure that includes a first boronic acid group attached by a first linker group to a first tertiary amine. The first tertiary amine is attached to a reporter group that includes an organometalic reporter moiety. A spacer group attaches the first tertiary amine to a second tertiary amine. The second tertiary amine is attached to an R group and a second linker group. The second linker group is attached to a second boronic acid group. In preferred embodiments, the compound selectively detects glucose and has a higher relative stability constant for glucose than for other saccharides.

20 Claims, 7 Drawing Sheets

ELECTROCHEMICAL SACCHARIDE SENSOR

CROSS-REFERENCE TO RELATED APPLICATIONS

This application is a continuation in part of U.S. patent application Ser. No. 09/729,332, filed Dec. 4, 2000, now U.S. Pat. No. 6,387,672 B1, by Tony James and Susumu Arimori, entitled "Photo-Induced Electron Transfer Fluorescent Sensor Molecules"; the contents of which are of which are hereby incorporated by reference in their entirety.

BACKGROUND

The following description provides a summary of information relevant to the present invention and is not a concession that any of the information provided or publications referenced herein is prior art to the presently claimed invention.

Saccharides, more commonly known as sugars, are organic compounds that play important roles in living organisms. Of particular medical and clinical interest is the monosaccharide D-glucose, which is a critical biochemical energy source for cells. Glucose is stored in the liver as glycogen, and is released as needed for energy consumption. The production and the consumption of glucose are regulated such that the concentration of glucose is relatively constant in the body fluids of a normal or healthy mammals. A disruption of this regulation of glucose can be associated with diseases such as diabetes and adrenal insufficiency in humans.

The detection of glucose in the blood or the urine provides valuable information for the diagnosis of these diseases. Electrochemical detection of saccharides by enzymatic decomposition of saccharides is known. One particular assay utilizes the enzyme glucose oxydase, which decomposes glucose to release hydrogen peroxide. The hydrogen peroxide can be measured by an electrode. A problem with this assay is that the enzymatic activity of the naturally occurring enzyme degrades with time. Thus the sample cannot be recycled for repeated assays because the glucose and enzyme have degraded. Further, this susceptibility to degradation makes the assay vulnerable to imprecision.

Recent approaches to detect saccharides involve the use of synthetic molecular receptors that bind to saccharides and exhibit a non-enzymatic chemically detectable change upon binding with the saccharide. Specifically, receptor molecules that incorporate boronic acid moieties have been shown to bind to saccharides through covalent interactions in aqueous basic media. The most common interaction is with cis-1,2- or 1,3-diols of saccharides to form five- or six-membered rings respectively.

Recently, a simple boronic acid receptor was reported that binds and detects sorbitol, fructose, and glucose by electrochemical changes. "Redox switching of carbohydrate binding to ferrocene boronic acid", A. N. J. Moore, D. D. M. Wayner, *Canadian Journal of Chemistry*—Revue Canadienne De Chimie, 77, 681 (1999). This monoboronic acid receptor exhibited selectivity for D-fructose. This is consistent with early reports that monoboronic acids have an inherent selectivity for D-fructose. "Polyol complexes and structure of the benzeneboronate ion" J. P. Lorand, J. D. Edward, *Journal of Organic Chemistry* 1959, 24, 769.

Although glucose may be detected electrochemically the above receptor, the receptor is not selective for glucose and the presence of other saccharides will interfere with any assay utilizing such a receptor. Unfortunately, the most common glucose measurement applications use complex samples such as plasma and the large number of interfering compounds make electrochemical determinations very difficult if not impossible. What is needed is a selective molecular receptor system for detecting glucose having the specificity required for clinical assays of complex samples.

SUMMARY

The invention satisfies this need. The invention provides compounds for detecting sacchharides by electrochemistry. The compounds comprise a first boronic acid group attached by a first linker group to a first tertiary amine, the first tertiary amine attached to a reporter group comprising an organometalic reporter moiety, the first tertiary amine further attached by a spacer group to a second tertiary amine, the second tertiary amine attached to an R group and a second linker group, and the second linker group attached to a second boronic acid group. In preferred embodiments, the compound selectively detects glucose and has a higher stability constant for glucose than for other saccharides The invention includes a method for detecting saccharides in a sample comprising the steps of providing a compound of the invention; treating the sample with the compound; and detecting saccharides bound to the compound. In a preferred embodiment, the compound has the formula herein below and the method for detecting saccharides selectively detects glucose.

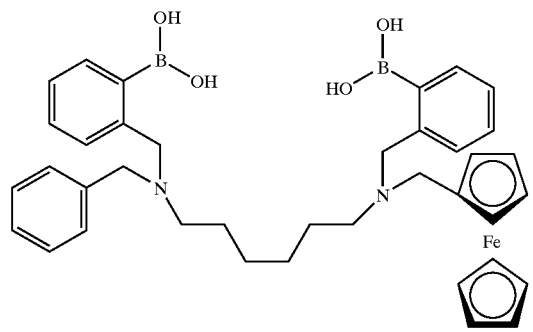

DRAWINGS

These features, aspects and advantages of the present invention will become better understood with regard to the following description, appended claims and accompanying figures where:

Figure 4:
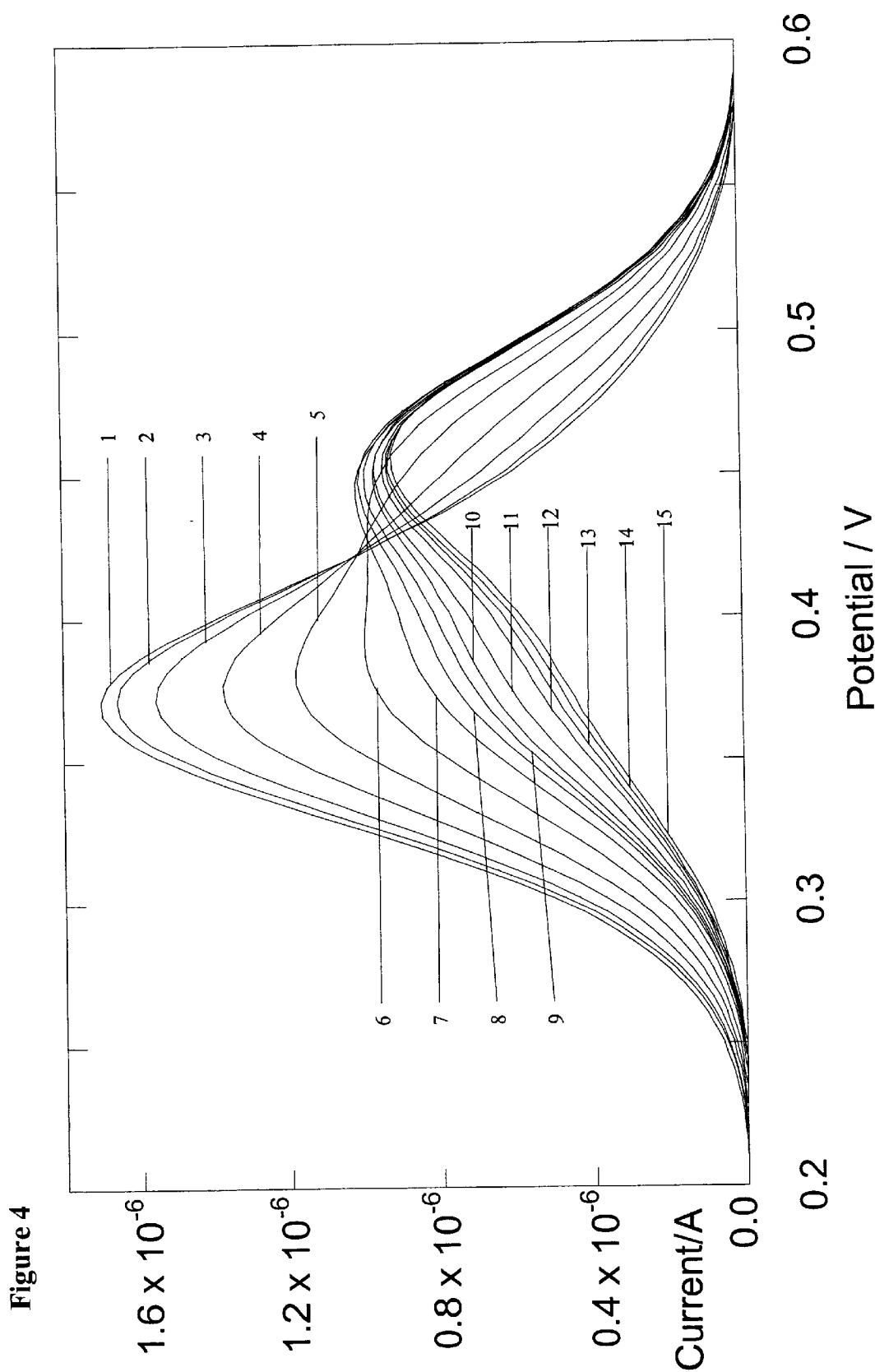

FIG. 4 illustrates a Differential Pulse Voltammogram (DPV) plot of compound 1 in the presence of concentrations of glucose ranging from 0–0.1 mol dm$^{-3}$. The D-glucose concentration for each of the curves from top to bottom are the following: 0/mol dm$^{-3}$ (curve 1), 1.11×10$^{-4}$/mol dm$^{-3}$ (curve 2), 3.89×10$^{-4}$/mol dm$^{-3}$ (curve 3), 6.66×10$^{-4}$/mol dm$^{-3}$ (curve 4), 1.04×10$^{-3}$/mol dm$^{-3}$ (curve 5), 2.04×10$^{-3}$/mol dm$^{-3}$ (curve 6), 3.79×10$^{-4}$/mol dm$^{-3}$ (curve 7), 6.01× 10$^{-3}$/mol dm$^{-3}$ (curve 8), 8.18×10$^{-3}$/mol dm$^{-3}$ (curve 9), 1.03×10$^{-2}$/mol dm$^{-3}$ (curve 10), 2.03×10$^{-2}$/mol dm$^{-3}$ (curve 11), 3.96×10$^{-2}$/mol dm$^{-3}$ (curve 12), 6.19×10$^{-2}$ mol dm$^{-3}$ (curve 13), 8.31×10$^{-2}$/mol dm$^{-3}$ (curve 14), and 1.0×10$^{-1}$/mol dm$^{-3}$ (curve 15).

Figure 5:
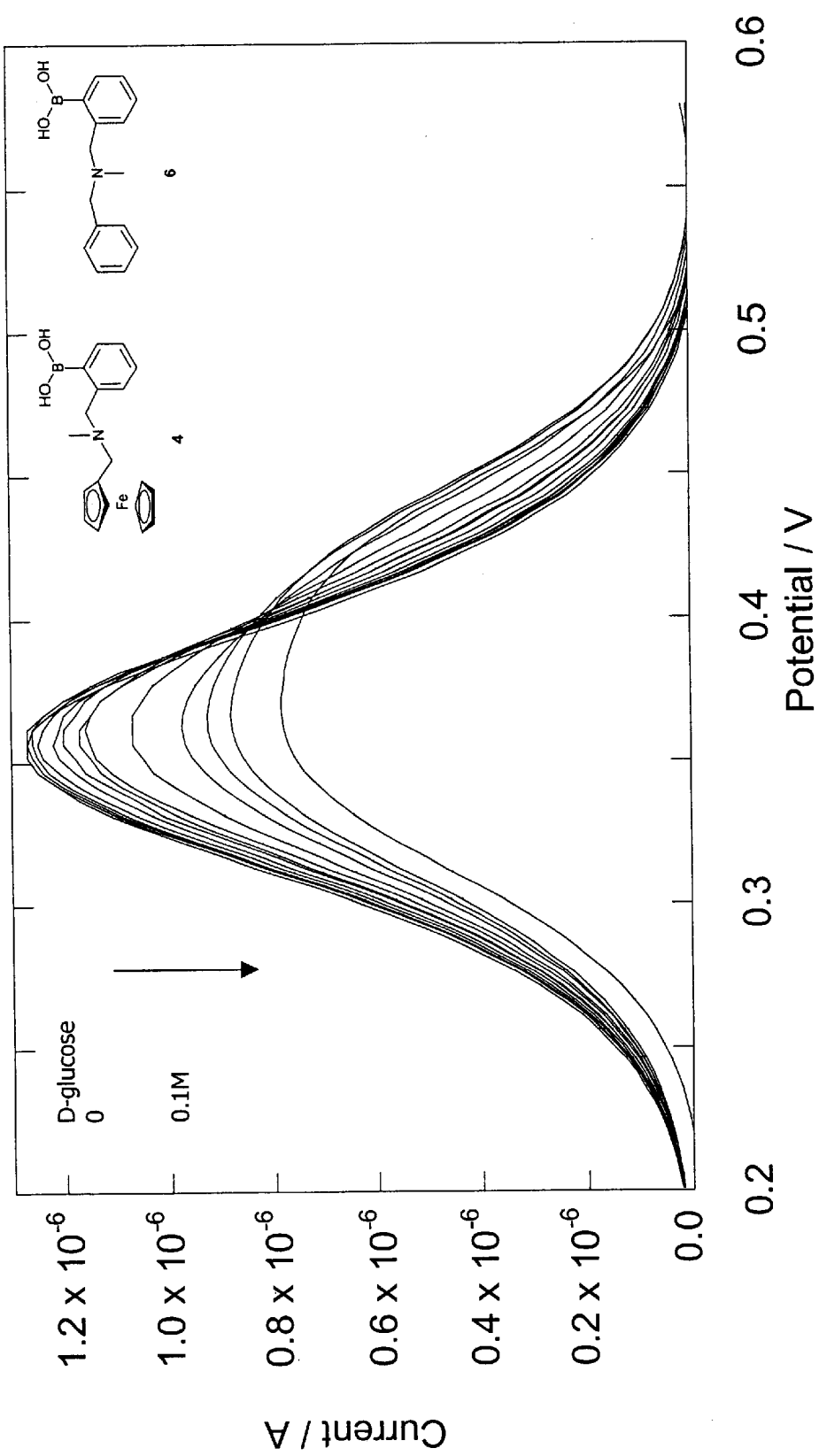
Figure 6:
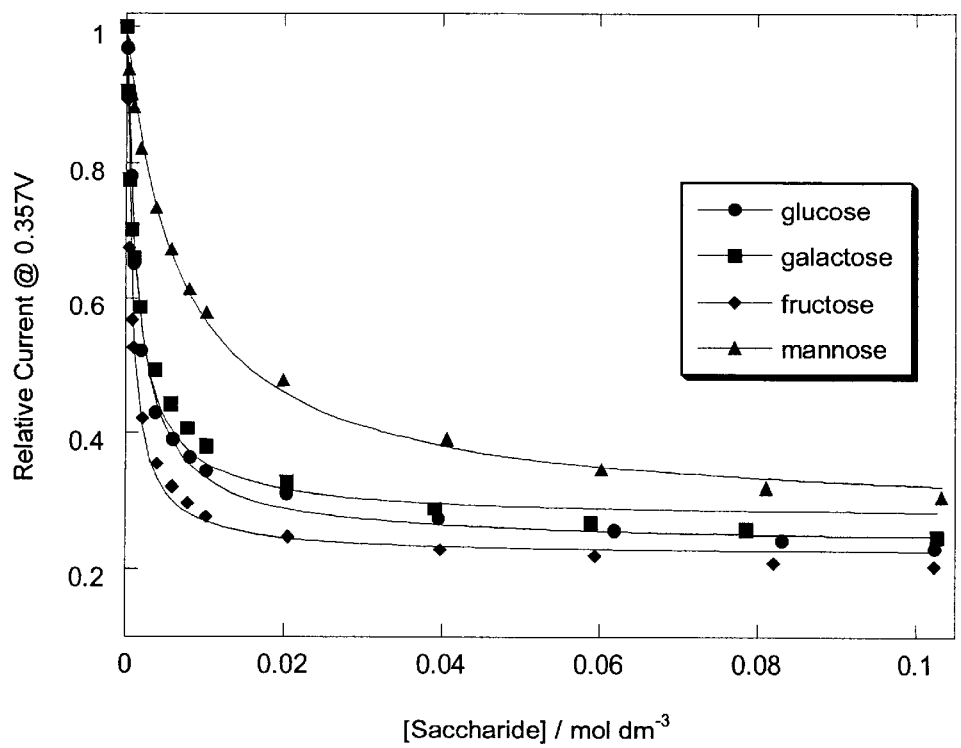
Figure 7:
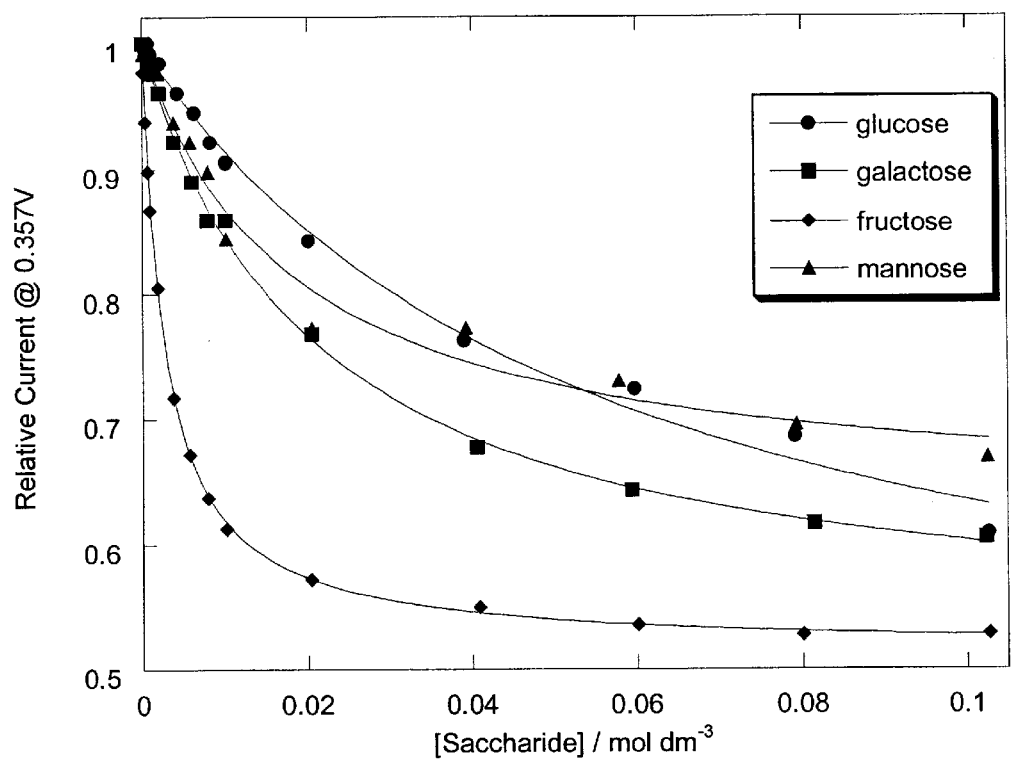

FIG. 5 illustrates a Differential Pulse Voltammetry spectra of compound 4 and compound 6 in the presence of increasing concentrations of glucose. The D-glucose curves were not numbered due to their proximity. The concentration for each of the curves from top to bottom are the following: 0/mol dm$^{-3}$, 1.11×10$^{-4}$/mol dm$^{-3}$, 4.07×10$^{-4}$/mol dm$^{-3}$, 6.66×10$^{-4}$/mol dm$^{-3}$, 1.02×10$^{-3}$/mol dm$^{-3}$, 2.15×10$^{-3}$/mol dm$^{-3}$, 4.27×10$^{-3}$, 6.33×10$^{-3}$/mol dm$^{-3}$, 8.31×10$^{-3}$/mol dm$^{-31}$ ₃, 1.02×10$^{-2}$/mol dm$^{31}$ ³, 2.00×10$^{-2}$/mol dm$^{-3}$, 3.90×10$^{-2}$/mol dm$^{-3}$, 5.97×10$^{-2}$/mol dm$^{-3}$, 7.91×10$^{-2}$/mol dm$^{-3}$, 1.02×10$^{-1}$/mol dm$^{-3}$;

FIG. 6 illustrates a plot of relative current vs. saccharide concentration for compound 1 (5.0×10$^{-5}$ mol dm$^{-3}$ each) for glucose, galactose, fructose, and mannose measured in 52.1 wt % MeOH at pH 8.21 (phosphate buffer); and FIG. 7 illustrates a plot of relative current vs. saccharide concentration for compound 4 and compound 6 (5.0×10$^{-5}$ mol dm$^{-3}$) for glucose, galactose, fructose, and mannose measured in 52.1 wt % MeOH at pH 8.21 (phosphate buffer).

DESCRIPTION

The following discussion describes embodiments of the invention and several variations of these embodiments. This discussion should not be construed, however, as limiting the invention to those particular embodiments. Practitioners skilled in the art will recognize numerous other embodiments as well. In all of the embodiments described herein that are referred to as being preferred or particularly preferred, these embodiments are not essential even though they may be preferred.

Structure of Glucose Sensing Compounds

The compounds of the invention are useful for detecting saccharrides, and in particular for detecting glucose. In preferred embodiments, the chemical structure of the compounds is such that they selectively detect glucose because they form complexes with glucose that have a higher stability constant than complexes formed with other saccharides. This glucose selectivity is accomplished by providing diboronic acid compounds and systems that control saccharide selectivity through two point binding.

The compounds of the invention comprise a first boronic acid group that is attached by a first linker group to a first tertiary amine. The first tertiary amine is attached to a reporter group comprising an organometalic reporter moiety. The first tertiary amine is additionally attached by a spacer group to a second tertiary amine. The second tertiary amine is attached to an R group and a spacer group. The spacer group is attached to a second boronic acid group.

In typical embodiments, the first linker comprises an aromatic ring, heteroaromatic ring, alkyl group, alkene group, or alkyne group. The presence of an amine group proximal to the boronic acid facilitates the binding of the compound to saccharides at a relatively a neutral pH. The interaction of a boronic acid (Lewis acid) and neighboring tertiary amine (Lewis base) is strengthened on saccharide binding. Conversely, simple boronic acids typically only bind saccharides at a high pH.

Although the spacer group may comprises a straight, branched, or cyclic structure, in the preferred embodiment the spacer is a straight chained alkyl group. Typically the spacer group comprises 1 to 10 carbon atoms, but spacers of larger length may also be used to match the size of various desired analytes. In a preferred embodiment, the number of carbons is 6 and the spacer group comprises hexamethylene. This compound has a higher stability constant with glucose than for other saccharides that enables the compound to selectively detect glucose.

Preferably, the R group comprises hydrogen, an akyl, an aryl, or a reporter group comprising an organometalic reporter moiety. Preferably, the second linker group comprises an aromatic ring, heteroaromatic ring, alkyl group, alkene group, or alkyne group. In a preferred embodiment, the organometalic reporter moiety comprises ferrocene or a ferrocene derivative.

Typical embodiments of a compound falling within the chemical structure of the present invention can be expressed by the general formula:

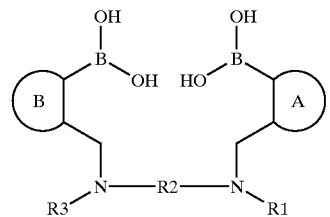

where the first linker group (A) comprises an aromatic ring or heteroaromatic ring; the reporter group (R1) comprises an organometalic reporter group; the spacer group (R2) comprises an akyl or an aryl; R3 comprises hydrogen, an akyl, an aryl, or a organometalic reporter group; and the second linker group (B) comprises an aromatic ring or heteroaromatic ring. Preferred embodiments have one or more of the following specific chemical groups: the spacer group (R2) is an alkyl group; the R1 and R3 groups are independently selected from the group consisting of hydrogen, an akyl, an aryl, and a reporter group comprising an organometalic reporter moiety; the organometalic reporter moiety comprises ferrocene or a ferrocene derivative. In a further preferable embodiment, the spacer group (R2) comprises hexamethylene.

Embodiments of compounds falling within the chemical structure of the present invention can further be expressed by the general formula:

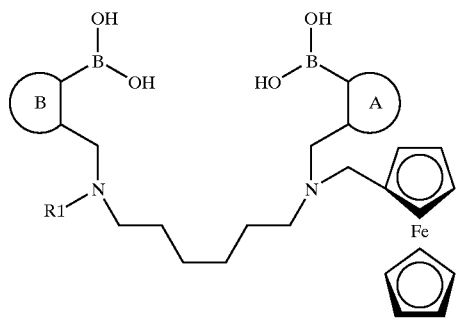

where A represents an aromatic ring or heteroaromatic ring; R1 is selected from the group consisting of hydrogen, an akyl, an aryl, and a organometalic reporter group; and B is an aromatic ring or heteroaromatic ring. This compound has a higher stability constant for glucose than for other saccharides that confers a selective detection of glucose relative to other sacharides.

Figure 1:
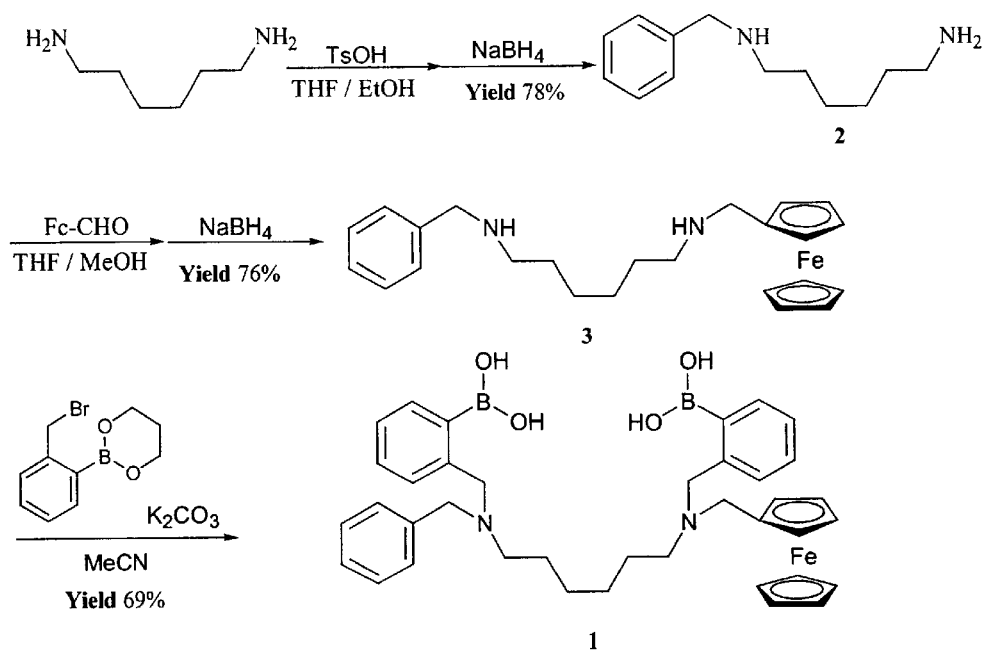
FIG. 1 illustrates a method of preparing an electrochemical glucose-sensing compound according to the invention.

In a particularly preferred embodiment the compound comprises the chemical formula (1), and again the compound has a higher stability constant for glucose than for other saccharides that allows it to selectively detect glucose. The preparation of compound 1, referred to herein as N-benzyl-N,N'-bis (2-boronobenzyl)-N'-ferrocenylmethyl hexamethyl-1, 6-diamine, is illustrated in FIG. 1 and is explained in detail in Examples I, II, and III.

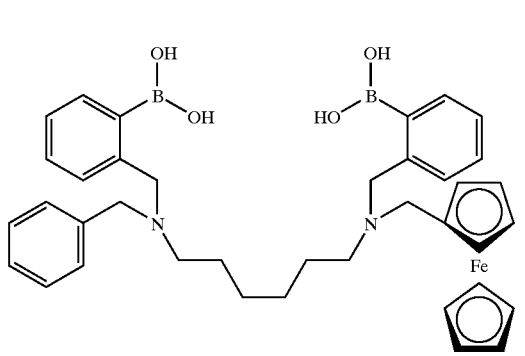

(1)

Methods for Detecting Glucose and Determining Stability Constants

The glucose in the sample is detected by determining glucose sensing compound bound to glucose. The redox potential of the organometalic reporter moiety of compound changes upon binding to a saccharide.

Redox potentials can be measured using a variety of standard electrochemical techniques such as cyclic voltammogram (CV) and pulse Voltammetry, including Tast polarography, Normal pulse voltammetry (NPV), Differential pulse voltammetry (DPV), Square-wave voltammery (SWV), Reverse pulse Voltammetry (RPV), Differential normal pulse voltammetry (DNPV), and Double differential pulse voltammetry (DDPV). These techniques are well known in the art. See for example C. M. A. Brett and A. M. Oliviera Brett, "Electrochemistry", Oxford university press, 1993, incorporated herein by reference. Electrochemical detection by Differential Pulse Voltammetry (DPV) is described in detail in Example VIII. FIG. 4 illustrates Differential Pulse Voltammogram (DPV) curves of compound 1 in the presence of different concentrations of D-glucose.

In order to investigate binding selectivity of compound 1 with various saccharides, the stability constant of compound 1 with particular saccharides was compared to the stability constant of monoboronic acids that are relatively non-specific with the same saccharides. The non-specific monobornic acids illustrated below were used for determining and comparing the relative binding affinity of the glucose sensing compound to glucose and other saccharides.

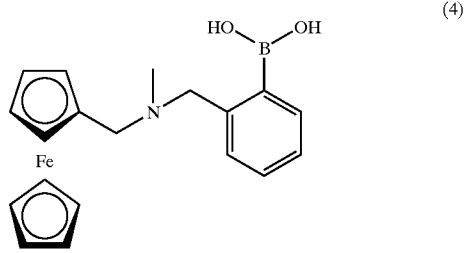

(4)

Figure 2:
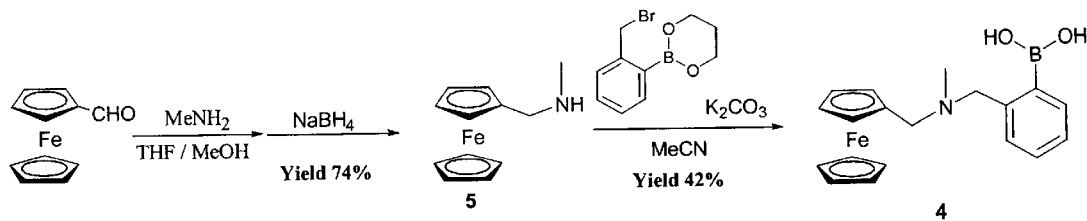
FIG. 2 illustrates a method of preparing an electrochemical saccharide-sensing compound.

The preparation of compound 4, referred to herein as N-(2-borinobenzyl)-N-methyl ferrocenyl methylamine (4), is illustrated in FIG. 2 and is explained in detail in the Example

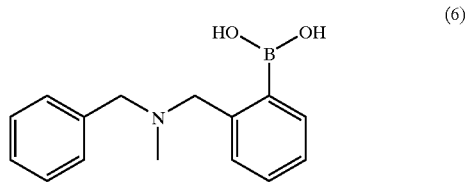

(6)

Figure 3:
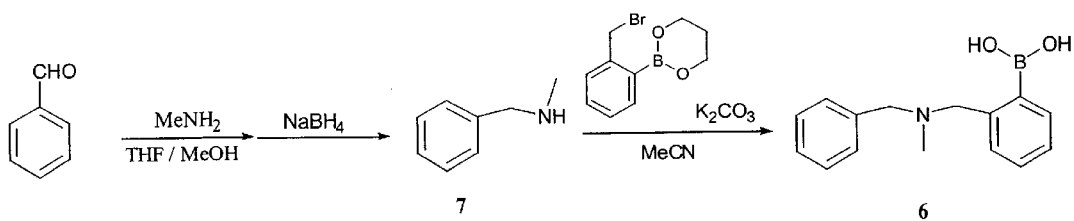
FIG. 3 illustrates a method of preparing a saccharide-sensing compound.

The preparation of compound 6, referred to herein as N-(2-borinobenzyl)-N-methyl benzylamine 6, is illustrated in FIG. 3 and is explained in detail in the Example VII.

FIG. 5 illustrates Differential Pulse Voltammetry curves of compound 4 and to compound 6 in the presence of increasing concentrations of glucose. FIGS. 4 and 5 show that as the amount of saccharide increases the relative current indicated by the amplitude of curve decreases. It is apparent from these two Figures that the observed changes in current in response to higher concentrations of glucose is greater in compound 1 shown in FIG. 4 than in compounds 4 and 6, shown in FIG. 5.

In FIG. 4, the glucose concentration {D-glucose} from top curve to bottom curve are as follows: 0/mol dm$^{-3}$ (curve 1), $1.11 \times 10^{-4}$/mol dm$^{-3}$ (curve 2), $3.89 \times 10^{-4}$/mol dm$^{-3}$ (curve 3), $6.66 \times 10^{-4}$/mol dm$^{-3}$ (curve 4), $1.04 \times 10^{-3}$/mol dm$^{-3}$ (curve 5), $2.04 \times 10^{-3}$/mol dm$^{-3}$ (curve 6), $3.79 \times 10^{-3}$/mol dm$^{-3}$ (curve 7), $6.01 \times 10^{-3}$/mol dm$^{-3}$ (curve 8), $8.18 \times 10^{-3}$/mol dm$^{-3}$ (curve 9), $1.03 \times 10^{-2}$/mol dm$^{-3}$ (curve 10), $2.03 \times 10^{-2}$/mol dm$^{-3}$ (curve 11), $3.96 \times 10^{-2}$/mol dm$^{-3}$ (curve 12), $6.19 \times 10^{-2}$/mol dm$^{-3}$ (curve 13), $8.31 \times 10^{-2}$/mol dm$^{-3}$ (curve 14), and $1.0 \times 10^{-1}$/mol dm$^{-3}$ (curve 15). In FIG. 5, the glucose concentration {D-glucose} from top curve to bottom curve are as follows: 0, $1.11 \times 10^{-4}$ $4.07 \times 10^{-4}$ $6.66 \times 10^{-4}$ $1.02 \times 10^{-3}$, $4.27 \times 10^{-3}$, $6.33 \times 10^{-3}$, $8.31 \times 10^{-3}$, $1.02 \times 10^{-2}$, $2.00 \times 10^{-2}$, $3.90 \times 10^{-2}$, $5.97 \times 10^{-2}$, $7.91 \times 10^{-2}$, $1.02 \times 10^{-1}$/mol dm$^{-3}$. This data indicates that compound 1 is more sensitive to changing glucose concentrations than compounds 4 and 6.

FIG. 6 is a plot of relative current to saccharide concentration for glucose, galactose, fructose, and mannose, in the presence of compound 1. FIG. 7 is a plot of relative current to saccharide concentration for glucose, galactose, fructose, and mannose, in the presence of compounds 4 and 6. The data for FIG. 6 and FIG. 7 are summarized in

TABLE I

Plot data for Figure 6

| {D-glucose} / mol dm$^{-3}$ | Relative current @ 0.357 V | {D-galactose} / mol dm$^{-3}$ | Relative current @ 0.357 V | {D-fructose} / mol dm$^{-3}$ | Relative current @ 0.357 V | {D-mannose} / mol dm$^{-3}$ | Relative current @ 0.357 V |
|---|---|---|---|---|---|---|---|
| 0.00 | 1.000 | 0.00 | 1.000 | 0.00 | 1.000 | 0.00 | 1.000 |
| $1.11 \times 10^{-4}$ | 1.000 | $1.11 \times 10^{-4}$ | 1.000 | $1.11 \times 10^{-4}$ | 0.977 | $1.11 \times 10^{-4}$ | 0.992 |
| $4.07 \times 10^{-4}$ | 1.000 | $4.07 \times 10^{-4}$ | 0.992 | $4.07 \times 10^{-4}$ | 0.938 | $4.26 \times 10^{-4}$ | 0.992 |
| $6.66 \times 10^{-4}$ | 1.000 | $7.40 \times 10^{-4}$ | 0.984 | $7.22 \times 10^{-4}$ | 0.898 | $6.66 \times 10^{-4}$ | 0.992 |
| $1.02 \times 10^{-3}$ | 0.992 | $9.99 \times 10^{-4}$ | 0.977 | $1.02 \times 10^{-3}$ | 0.867 | $9.99 \times 10^{-4}$ | 0.984 |
| $2.15 \times 10^{-3}$ | 0.984 | $2.00 \times 10^{-3}$ | 0.961 | $1.94 \times 10^{-3}$ | 0.805 | $1.94 \times 10^{-3}$ | 0.977 |
| $4.27 \times 10^{-3}$ | 0.961 | $3.83 \times 10^{-3}$ | 0.922 | $3.83 \times 10^{-3}$ | 0.717 | $3.87 \times 10^{-3}$ | 0.938 |
| $6.33 \times 10^{-3}$ | 0.945 | $6.01 \times 10^{-3}$ | 0.891 | $5.79 \times 10^{-3}$ | 0.672 | $5.88 \times 10^{-3}$ | 0.922 |
| $8.31 \times 10^{-3}$ | 0.921 | $7.86 \times 10^{-3}$ | 0.859 | $8.05 \times 10^{-3}$ | 0.637 | $8.03 \times 10^{-3}$ | 0.898 |
| $1.02 \times 10^{-2}$ | 0.906 | $1.01 \times 10^{-2}$ | 0.859 | $1.03 \times 10^{-2}$ | 0.613 | $1.02 \times 10^{-2}$ | 0.844 |
| $2.00 \times 10^{-2}$ | 0.843 | $2.04 \times 10^{-2}$ | 0.768 | $2.04 \times 10^{-2}$ | 0.572 | $2.05 \times 10^{-2}$ | 0.773 |
| $3.90 \times 10^{-2}$ | 0.763 | $4.05 \times 10^{-2}$ | 0.678 | $4.09 \times 10^{-2}$ | 0.549 | $3.93 \times 10^{-2}$ | 0.773 |
| $5.97 \times 10^{-2}$ | 0.724 | $5.94 \times 10^{-2}$ | 0.643 | $6.01 \times 10^{-2}$ | 0.535 | $5.78 \times 10^{-2}$ | 0.731 |
| $7.91 \times 10^{-2}$ | 0.686 | $8.14 \times 10^{-2}$ | 0.616 | $8.01 \times 10^{-2}$ | 0.527 | $7.93 \times 10^{-2}$ | 0.696 |
| $1.03 \times 10^{-1}$ | 0.608 | $1.02 \times 10^{-1}$ | 0.605 | $1.03 \times 10^{-1}$ | 0.528 | $1.03 \times 10^{-1}$ | 0.670 |

TABLE II

Plot data for Figure 7

| {D-glucose} / mol dm$^{-3}$ | Relative current @ 0.357 V | {D-galactose} / mol dm$^{-3}$ | Relative current @ 0.357 V | {D-fructose} / mol dm$^{-3}$ | Relative current @ 0.357 V | {D-mannose} / mol dm$^{-3}$ | Relative current @ 0.357 V |
|---|---|---|---|---|---|---|---|
| 0.00 | 1.000 | 0.00 | 1.000 | 0.00 | 1.000 | 0.00 | 1.000 |
| $1.11 \times 10^{-4}$ | 1.000 | $1.11 \times 10^{-4}$ | 1.000 | $1.11 \times 10^{-4}$ | 0.977 | $1.11 \times 10^{-4}$ | 0.992 |
| $4.07 \times 10^{-4}$ | 1.000 | $4.07 \times 10^{-4}$ | 0.992 | $4.07 \times 10^{-4}$ | 0.938 | $4.26 \times 10^{-4}$ | 0.992 |
| $6.66 \times 10^{-4}$ | 1.000 | $7.40 \times 10^{-4}$ | 0.984 | $7.22 \times 10^{-4}$ | 0.898 | $6.66 \times 10^{-4}$ | 0.992 |
| $1.02 \times 10^{-3}$ | 0.992 | $9.99 \times 10^{-4}$ | 0.977 | $1.02 \times 10^{-3}$ | 0.867 | $9.99 \times 10^{-4}$ | 0.984 |
| $2.15 \times 10^{-3}$ | 0.984 | $2.00 \times 10^{-3}$ | 0.961 | $1.94 \times 10^{-3}$ | 0.805 | $1.94 \times 10^{-3}$ | 0.977 |
| $4.27 \times 10^{-3}$ | 0.961 | $3.83 \times 10^{-3}$ | 0.922 | $3.83 \times 10^{-3}$ | 0.717 | $3.87 \times 10^{-3}$ | 0.938 |
| $6.33 \times 10^{-3}$ | 0.945 | $6.01 \times 10^{-3}$ | 0.891 | $5.79 \times 10^{-3}$ | 0.672 | $5.88 \times 10^{-3}$ | 0.922 |
| $8.31 \times 10^{-3}$ | 0.921 | $7.86 \times 10^{-3}$ | 0.859 | $8.05 \times 10^{-3}$ | 0.637 | $8.03 \times 10^{-3}$ | 0.898 |
| $1.02 \times 10^{-2}$ | 0.906 | $1.01 \times 10^{-2}$ | 0.859 | $1.03 \times 10^{-2}$ | 0.613 | $1.02 \times 10^{-2}$ | 0.844 |
| $2.00 \times 10^{-2}$ | 0.843 | $2.04 \times 10^{-2}$ | 0.768 | $2.04 \times 10^{-2}$ | 0.572 | $2.05 \times 10^{-2}$ | 0.773 |
| $3.90 \times 10^{-2}$ | 0.763 | $4.05 \times 10^{-2}$ | 0.678 | $4.09 \times 10^{-2}$ | 0.549 | $3.93 \times 10^{-2}$ | 0.773 |
| $5.97 \times 10^{-2}$ | 0.724 | $5.94 \times 10^{-2}$ | 0.643 | $6.01 \times 10^{-2}$ | 0.535 | $5.78 \times 10^{-2}$ | 0.731 |
| $7.91 \times 10^{-2}$ | 0.686 | $8.14 \times 10^{-2}$ | 0.616 | $8.01 \times 10^{-2}$ | 0.527 | $7.93 \times 10^{-2}$ | 0.696 |
| $1.03 \times 10^{-1}$ | 0.608 | $1.02 \times 10^{-1}$ | 0.605 | $1.03 \times 10^{-1}$ | 0.528 | $1.03 \times 10^{-1}$ | 0.670 |

The Differential Pulse Voltammograms of these compounds were used to calculate the stability constant for each compound with a specific saccharide. The stability constant K for the saccharide complexes was calculated according to the following equation.

$$I_C = (I_{C0} + I_{Cf} \times K \times \{guest\})/(1 + K \times \{guest\})$$

Where $I_{C0}$ is the initial (minimum) current intensity; $I_{Cf}$ is the final (maximum) current intensity; $I_C$ is the current intensity for a particular concentration of guest saccharide; K is the stability constant of the receptor with the guest; {guest} is the concentration of the guest; described in Fery-Forgues, S. et al., "Ion-responsive fluorescent compounds. 1. Effect of cation binding on photophysical properties of a benzoxazione derivative linked to monoaza-15-crown-5", J. Phys. Chem., 1988, 92, 6233–6237, incorporated herein by reference. The 'guest' is the analyte of interest, which is the particular saccharide being examined.

The stability constant (K) curves were analyzed in KaleidaGraph using nonlinear (Levenberg-Marquardt algorithm) curve fitting of equations (1). The errors reported are the standard errors ($\pm s/\sqrt{N}$) obtained from the best fit. KaleidaGraph Version 3.08d for the Macintosh, Published by Synergy Software and Developed by Abelbeck Software (Reading, Pa.). A user defined curve fit (1+m2* ml * (M0))/(1+ml * (M0)) derived from equations (1) was used in all calculations. The Initial value of ml (K) was set to 1 and the initial value of m2 ($I_{Cf}$) was set to 0.9. The variable (M0) was {guest}. The allowable error was set to 0.001%. For all curves the coefficient of determination ($r^2$) was >0.99.

Table III presents data including the stability constants (K) for complexes of two electrochemical sensors with particular saccharides, which are listed in column 1. Column two of Table III includes the absolute stability constants determined for compound 1 with glucose, galactose, fructose, and mannose. Column three of Table III includes the absolute stability constants determined for the non-selective intermolecular system of compounds 4 plus 6 with glucose, galactose, fructose, and mannose. The fourth column presents the relative stability constants, which are derived by dividing the absolute stability constant of compound 1 for each particular saccharide by the absolute stability constant for binding with compounds 4 plus 6 in the presence of the same saccharide. The data demonstrates that compound 1 has a relative stability constant for glucose that is at least two times higher in comparison with other saccharides. Also, the relative stability constant of compound 1 to glucose is typically between about 2 and about 15 times greater than the relative stability constant of compound 1 with the other saccharides presented in Table III. This higher stability constant confers the relative specificity of compound 1 for glucose.

TABLE III

| Saccharide | 1 K | 4 + 6 K | 1/(4 + 6) K Relative |
|---|---|---|---|
| D-glucose | 684 ± 54 (1.00) | 17 ± 2 (1.00) | 40 |
| D-galactose | 781 ± 72 (0.99) | 47 ± 2 (1.00) | 17 |
| D-fructose | 1478 ± 72 (1.00) | 362 ± 5 (1.00) | 4 |
| D-mannose | 149 ± 9 (1.00) | 54 ± 8 (1.00) | 3 |

EXAMPLE I

Preparation of N-benzyl-hexane-1,6-diamine (2)

A solution of benzaldehyde (1.0 ml, 10.0 mmol) in THF (50 ml) was added with heating at reflux to a solution of 1,6-diaminohexane (5.81 g, 50.0 mmol) and p-toluene sulfonic acid (9.5 1 g, 50.0 mmol) in ethanol (50 ml) and then it was heated to reflux for 3 h under a nitrogen atmosphere. After cooling to room temperature, sodium borohydride (1.13 g, 30.0 mmol) was added to the solution and it was stirred at room temperature for 1 h. The solvent was removed under reduced pressure and the residue dissolved in chloroform. The chloroform phase was washed with water, and dried over magnesium sulphate, the solvent was removed under reduced pressure. The residue was washed with water (25 ml), and it dissolved in chloroform and washed again with water (2×50 ml). Then dried over magnesium sulphate, and the solvent removed under reduced pressure to yield a yellow oil (1.61 g, 78%).

$\delta_H$ (300 MHz, CDCl$_3$, Me$_4$Si): 1.1–1.5 (8H, m, (CH$_2$)$_4$), 2.55 (2H, t, NHCH$_2$), 2.65 (2H, t, ArCNCH$_2$), 3.75 (2H, s, ArCH$_2$), 7.15–7.25 (5H, m, Ar—H). $\delta_C$ (75 MHz, CDCl$_3$, Me$_4$Si): 26.9, 27.3, 30.2, 33.8, 42.2, 49.4, 54.1, 126.7, 127.9, 128.2, 140.4.

EXAMPLE II

Preparation of N-benzyl-N'-ferrocenylmethyl-hexamethylene-1,6-diamine (3)

A solution of 2 (600 mg, 2.91 mmol) and ferrocenecarboxyaldehyde (747 mg, 3.49 mmol) in THF and methanol (15 ml each) was stirred at room temperature for 7 h under nitrogen atmosphere. Sodium borohydride (396 mg, 10.5 mmol) was added to this solution and then it was stirred at room temperature for 1 h. The solvent was removed under reduced pressure, and the residue dissolved in chloroform. The chloroform phase was washed with water, and dried over magnesium sulphate and the solvent was removed under reduced pressure. The residue was purified by gel filtration {Sephadex LH-20, using methanol as eluent} to yield an orange oil (892 mg, 76%).

$\delta_H$ (300 MHz, CDCl$_3$, Me$_4$Si): 1.33 (4H, bs, NCC(CH$_2$)$_2$), 1.49 (4H, bs, NC(CH$_2$)$_2$) 2.61 (2H, t, FcCNCH$_2$), 2.62 (2H, t, NCH$_2$), 3.50 (2H, s, NCH$_2$Fc), 3.78 (2H, s, PhCH$_2$N), 4.09–4.12 and 4.18 (5H, 4H, m each, Fc-H), 7.34 (5H, m, Ar—H); $\delta_C$ (75 MHz, CDCl$_3$, Me$_4$Si): 27.4, 30.2, 49.1, 49.5, 49.6, 54.1, 67.7, 68.3, 68.4, 126.7, 128.0, 128.2, 140.4.

EXAMPLE III

Preparation of N-benzyl-N,N'-bis(2-boronobenzyl)-N'-ferrocenylmethyl hexamethyl-1, 6-diamine (1)

A solution of 3 (800 mg, 1.98 mmol), potassium carbonate (1.10 g, 7.92 mmol), and 2-(2-bromobenzyl) 1,3,2-dioxaborinane (1.21 g, 4.72 mmol) in acetonitrile (35 ml) was heated to reflux for 7h under a nitrogen atmosphere. The solvent was removed under reduced pressure, and the residue dissolved in chloroform. The chloroform phase was washed with water and dried over magnesium sulphate, and the solvent was removed under reduced pressure. The residue was reprecipitated from chloroform and n-hexane to yield a yellow powder (920 mg, 69%).

mp 155–158° C. (decomp); m/z (FAB) 1212 ({M+H+4 (3-HOCH$_2$C$_6$H$_4$NO$_2$)-4H$_2$O}$^+$, 95% ; Found: C, 69.25; H, 7.07; N, 4.12%. C$_{38}$H$_{46}$B$_2$FeN$_2$O$_4$—H$_2$O+0.05 CHCl$_3$ requires C, 69.21; H, 6.74; N, 4.24%. $\delta_H$ (300 MHz, CDCl$_3$+CD$_3$OD (a few drops), Me$_4$Si): 1.28 (4H, bs, NCC(CH$_2$)$_2$), 1.42 (4H, bs, NC(CH$_2$)$_2$), 2.28 (2H, t, FcCNCH$_2$), 2.36 (2H, tNCH$_2$), 3.56 (4H, s, NCH$_2$Ph), 3.58 (2H, s, FcCH$_2$N), 3.78 (2H, s, NCH$_2$Ph), 4.12 and 4.18 (5H, 4H, s each, Fc-H), 7.15–7.38, 7.86 (11H, 2H, m each, Ar—H). $\delta_C$ (75 MHz, CDCl$_3$+CD$_3$OD (a few drops), Me$_4$Si): 22.7, 24.7, 25.6, 27.0, 31.6, 51.2, 52.0, 57.1, 60.4, 61.3, 68.4, 68.5, 68.6, 68.9, 70.6, 127.2, 127.3, 127.5, 128.2, 128.5, 129.6, 129.7, 129.9, 130.6, 130.9, 136.2, 136.5, 141.7, 141.8.

EXAMPLE IV

Preparation of N-methyl ferrocenylmethylamine (5)

A solution of ferrocenecarboxaldehyde (700 mg, 3.27 mmol) and methylamine (2.0M in THF) (5.0 ml, 10.0 mmol) in THF (25 ml) and methanol (30 ml) was stirred at room temperature for 15 h under a nitrogen atmosphere. Sodium borohydride (371 mg, 9.81 mmol) was added to the solution and it was stirred at room temperature for 1 h. The solvent was removed out under reduced pressure and the residue dissolved in chloroform. The chloroform was washed with water, dried over magnesium sulphate. The solvent was removed under reduced pressure to yield a brown oil (647 mg, 86%).

$\delta_H$ (300 MHz, CDCl$_3$, Me$_4$Si): 2.48 (3H, s, NCH$_3$), 3.47 (2H, s, NCH$_2$), 4.12–4.18 (9H, m, Fc-H); $\delta_C$ (75 MHz, CDCl$_3$, Me$_4$Si): 36.6, 51.5, 68.1, 68.3, 68.7, 68.8, 69.2, 69.6, 69.8, 70.8, 87.1.

EXAMPLE V

Preparation of N- (2-borinobenzyl)-N-methyl ferrocenyl methylamine (4)

A solution of 5 (250 mg, 1.09 mmol), potassium carbonate (301 mg, 2.18 mmol) and 2-(2-bromobenzyl)-1,3,2-dioxaborinane (333 mg, 1.31 mmol) in acetonitrile (10 ml) was heated to reflux for 5 h under a nitrogen atmosphere. The solvent was removed under reduced pressure, and the residue was dissolved in chloroform. The chloroform phase was washed with water, dried over magnesium sulphate. The solvent was removed under reduced pressure, the residue was reprecipitated from chloroform and n-hexane to yield a yellow powder (167 mg, 42%)

mp 130–134° C. (decomp); m/z (FAB) 633 ({M+H+2(3-HOCH$_2$C$_6$H$_4$NO$_2$)-2H$_2$O}$^+$, 58%; $\delta_H$ (300 MHz, CDCl$_3$+CD$_3$OD (a few drops), Me$_4$Si): 2.23 (3H, s, NCH$_3$), 3.40 (2H, s, NCH$_2$Fc), 3.51(2H, s, NCH$_2$), 4.12–4.18 (9H, m, Fc-H), 6.72–7.28 (4H, m, Ar—H); $\delta_C$ (75 MHz, CDCl$_3$+CD$_3$OD (a few drops), Me$_4$Si): 41.2, 55.4, 56.2, 68.7, 68.9, 69.1, 70.5, 114.7, 115.0, 117.0, 119.5, 127.4, 128.8.

EXAMPLE VI

Preparation of N-methyl benzylamine (7)

A solution of benzaldehyde (2.0 ml, 20.0 mmol) and methylamine (2.0M in THF) (20.0 ml, 40.0 mmol) and methanol (20 ml) was stirred at room temperature for 20 h under a nitrogen atmosphere. Sodium borohydride (2.27 g, 60.0 mmol) was added to the solution and it was stirred at room temperature for 2 h. The solvent was removed out under reduced pressure and the residue dissolved in chloroform. The chloroform was washed with brine, and dried over magnesium sulphate. The solvent was removed under reduced pressure to yield a yellow oil (1.32 g, 55%).

$\delta_H$ (300 MHz, CDCl$_3$, Me$_4$Si): 2.42 (3H, s, NCH$_3$), 3.74 (2H, s, NCH$_2$Fc), 7.20–7.38 (5H, m, Ar—H); $\delta_C$ (75 MHz, CDCl$_3$, Me$_4$Si): 36.0, 56.1, 127.0, 128.4, 129.1, 140.1.

EXAMPLE VII

Preparation of N-(2-borinobenzyl)-N-methyl benzylamine (6)

A solution of 7 (500 mg, 4.13 mmol), potassium carbonate (1.14 mg, 8.26 mmol) and 2-(2-bromobenzyl)-1,3,2- dioxaborinane (1.26 mg, 4.96 mmol) in acetonitrile (20 ml) was heated to reflux for 8 h under a nitrogen atmosphere. The solvent was removed under reduced pressure, and the residue was dissolved in chloroform. The chloroform phase was washed with brine, and dried over magnesium sulphate. The solvent was removed under reduced pressure, the residue was reprecipitated from chloroform and n-hexane to yield a yellow powder (105 mg, 10%)

mp 99–103° C.; $\delta_H$ (300 MHz, CD$_3$OD, Me$_4$Si): 2.71 (3H, s, NCH$_3$), 4.75 (2H, s, NCH$_2$), 4.80 (2H, s, ArBNCH$_2$), 7.10–7.68(9H, m, Ar—H); $\delta_C$ (75 MHz, CD$_3$OD, Me$_4$Si): 38.8, 58.8, 61.9, 125.7, 126.9, 128.1, 128.4, 129.0, 129.1, 130.4, 133.1, 135.1, 135.8

EXAMPLE VIII

Differential Pulse Voltammogram (DPV)

The DPV shown in FIG. 4 illustrates Differential Pulse Voltammogram (DPV) curves of compound 1 in the presence of concentrations of glucose ranging from 0–0.1 mol dm$^{-3}$. The D-glucose concentration for each of the curves from top to bottom are the following: 0/mol dm$^{-3}$, 1.1×10$^{-4}$/mol dm$^{-3}$, 3.9×10$^{-4}$/mol dm$^{-3}$, 6.7×10$^{-4}$/mol dm$^{-3}$, 1.0×10$^{-3}$/mol dm$^{-3}$, 3.8×10$^{-3}$/mol dm$^{-3}$, 6.0×10$^{-1}$/mol dm$^{-3}$, and 1.0×10$^{-1}$/mol dm$^{-3}$.

The measurement solution for the differential pulse voltammograms (DPV) was a aqueous methanolic buffer solution comprising 52.1 wt % methanol at pH 8.21, KCl, 0.01000 mol dm$^{-3}$; KH$_2$PO$_4$, 0.002752 mol dm$^{-3}$; and Na$_2$HPO$_4$, 0.002757 mol dm$^{-3}$. The measurements were preformed with 30 ml of the measurement solution in the measurement cell under nitrogen. The measurement temperature was room temperature (25° C.). The scanning conditions were the following: modulation time, 50 ms; interval time, 500 ms; step potential, 5.1 mV; modulation amplitude, 25.05 mV; initial potential, 0.1V; end potential, 0.6V.

The DPV was recorded with µAUTOLAB Type II (AUTOLAB Co.) using single-compartment cell fitted with a glassy carbon electrode for working electrode (0.28 cm$^2$), a platinum plate for counter electrode, and a Ag/AgCl reference electrode. The scanning conditions were modulation time, 50 ms; interval time, 500 ms; step potential, 5.1 mV; modulation amplitude 25.05 mV. The voltammogram, current intensity at 0.372 volt decreases with increasing saccharide concentration and a 0.450 volt species due to the bound species appears. The stability constant K with each saccharide were calculated by curve fitting the current intensity at 0.372 volt versus concentration of saccharide.

Having thus described the invention, it should be apparent that numerous modifications and adaptations may be resorted to without departing from the scope and fair meaning of the instant invention as set forth hereinabove and as described hereinbelow by the claims.

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. §112.

What is claimed is:

1. A compound comprising a first boronic acid group attached by a first linker group to a first tertiary amine, the first tertiary amine attached to a reporter group comprising an organometalic reporter moiety, the first tertiary amine further attached by a spacer group to a second tertiary amine, the second tertiary amine attached to an R group and a second linker group, and the second linker group attached to a second boronic acid group.

2. The compound of claim 1 wherein the first linker is selected from the group consisting of aromatic rings, heteroaromatic rings, alkyl groups, alkene groups, and alkyne groups.

3. The compound of claim 1 wherein the spacer group comprises an alkyl group.

4. The compound of claim 1 wherein the spacer group comprises hexamethylene.

5. The compound of claim 1 wherein the R group is selected from the group consisting of hydrogen, akyl groups, aryl groups, and a reporter group comprising an organometalic reporter moiety.

6. The compound of claim 1 wherein the second linker group is selected from the group consisting of aromatic rings, heteroaromatic rings, alkyl groups, alkene groups, and alkyne groups.

7. The compound of claim 1 wherein the organometalic reporter moiety is ferrocene or a ferrocene derivative and the compound binds and detects saccharides electrochemically.

8. The compound of claim 1 wherein the compound has a higher relative stability constant for glucose than for other saccharides.

9. The compound of claim 8, wherein the compound has a relative stability constant for glucose that is at least two times higher than the relative stability constant for the compound and other saccharides.

10. The compound of claim 8, wherein the compound has a relative stability constant for glucose that is between about two and about fifteen times greater than the relative stability constant for the compound and other saccharides.

11. A compound having the formula:

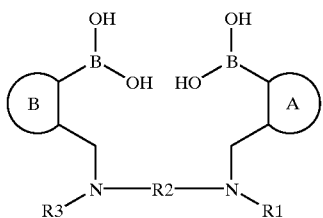

wherein A is an aromatic ring or heteroaromatic ring, R1 comprises an organometalic reporter group, R2 is a linker group comprising an akyl or an aryl, R3 comprises hydrogen, an akyl, an aryl, or a organometalic reporter group, and B is an aromatic ring or heteroaromatic ring.

12. A compound for detecting glucose having the formula:

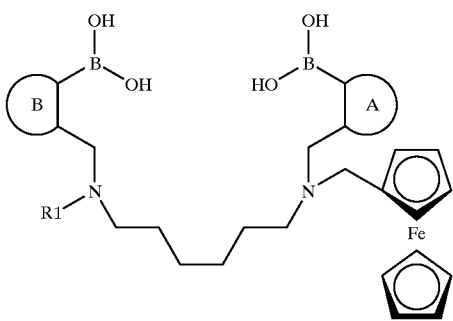

where A is an aromatic ring or heteroaromatic ring, R1 is selected from the group consisting of hydrogen, akyl groups, aryl groups, and a organometalic reporter group, and B is an aromatic ring or heteroaromatic ring.

13. The compound of claim 12, wherein the compound has a higher relative stability constant for glucose than for other saccharides.

14. The compound of claim 13, wherein the compound has a relative stability constant for glucose that is between about two and about fifteen times greater than the relative stability constant for the compound and other saccharides.

15. A compound for detecting glucose having the following formula:

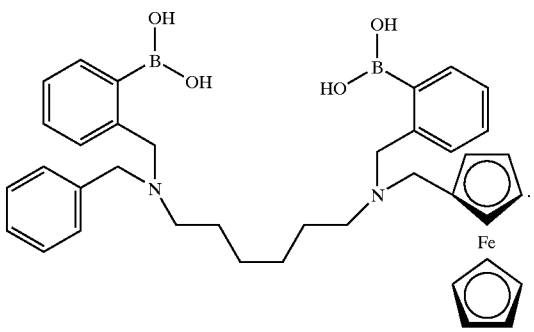

16. The compound of claim 15, wherein the compound has a relative stability constant for glucose that is between about two and about fifteen times greater than the relative stability constant for the compound and other saccharides.

17. An method for detecting saccharides in a sample comprising the steps of:
providing a predetermined amount of a compound selected from the group consisting of the compound of claim 1, the compound of claim 10, the compound of claim 11, the compound of claim 14, the compound of claim 15, or the compound of claim 16;
treating the sample with the compound; and
detecting saccharides bound to the compound.

18. The method of claim 17, wherein the method preferentially detects glucose relative to other saccharides.

19. The method of claim 17, wherein the compound is the compound of claim 1.

20. The method of claim 17, wherein the compound is the compound of claim 15 and the method preferentially detects glucose relative to other saccharides.

* * * * *